(12) United States Patent
Dorsel et al.

(10) Patent No.: US 6,406,849 B1
(45) Date of Patent: Jun. 18, 2002

(54) INTERROGATING MULTI-FEATURED ARRAYS

(75) Inventors: Andreas N. Dorsel, Menlo Park; Kyle J. Schleifer, Sunnyvale; Elecia C. White, San Jose; Charles S. Ladd, Union City; Debra A. Sillman, Santa Clara, all of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/430,214

(22) Filed: Oct. 29, 1999

(51) Int. Cl.⁷ .............................. C12Q 1/68; C12M 1/00; G01N 15/06; G01N 21/29; G01J 3/30
(52) U.S. Cl. .................. 435/6; 435/7.1; 435/283.1; 435/286.1; 435/287.1; 435/287.2; 435/288.7; 436/172; 422/50; 422/55; 422/68.1; 422/82.05; 356/317; 356/323; 356/375; 356/380; 356/398; 356/400; 356/401
(58) Field of Search ................... 435/4, 6, 7.1, 7.92, 435/283.1, 286.1, 287.1, 287.2, 288.7; 436/172; 356/317–320, 323, 326, 375, 380, 398, 400, 401, 244, 246; 422/50, 52, 55, 68.1, 82.05, 82.08

(56) References Cited

U.S. PATENT DOCUMENTS

| | | | | |
|---|---|---|---|---|
| 4,855,930 A | * | 8/1989 | Chao et al. ............ | 364/497 |
| 5,721,435 A | * | 2/1998 | Troll et al. ............ | 250/559.29 |
| 5,763,870 A | * | 6/1998 | Sadler et al. ............ | 250/209.2 |
| 5,998,141 A | * | 12/1999 | Acton ............ | 435/6 |
| 6,215,894 B1 | | 4/2000 | Zeleny et al. ............ | 382/133 |

OTHER PUBLICATIONS

Montagu, J. et al., "Fluorescence Array Scanner Employing a Flying Object", Journal of the Association for Laboratory Automation, vol. 4, No. 1, Mar. 1999, pp. 40–43.

* cited by examiner

Primary Examiner—Ardin H. Marschel
(74) Attorney, Agent, or Firm—Gordon M. Stewart

(57) ABSTRACT

A method, apparatus for executing the method, and computer program products for use in such an apparatus. The method includes scanning an interrogating light across multiple sites on an array package including an addressable array of multiple features of different moieties, which scanned sites include multiple array features. Signals from respective scanned sites emitted in response to the interrogating light are detected. The interrogating light power is altered for a first site on the array package during the array scan, based on location of the first site or on a determination that the emitted signal from the first site will be outside a predetermined value absent the altering (which allows for protecting a detector against expected overly bright sites), or is altered during the array scan based on the detected interrogating light power (which allows for compensating for light source drift during an array scan).

32 Claims, 3 Drawing Sheets

INTERROGATING MULTI-FEATURED ARRAYS

FIELD OF THE INVENTION

This invention relates to arrays, particularly biopolymer arrays such as DNA arrays, which are useful in diagnostic, screening, gene expression analysis, and other applications.

BACKGROUND OF THE INVENTION

Polynucleotide arrays (such as DNA or RNA arrays), are known and are used, for example, as diagnostic or screening tools. Such arrays include features (sometimes referenced as spots or regions) of usually different sequence polynucleotides arranged in a predetermined configuration on a substrate. The array is "addressable" in that different features have different predetermined locations ("addresses") on a substrate carrying the array.

Biopolymer arrays can be fabricated using in situ synthesis methods or deposition of the previously obtained biopolymers. The in situ synthesis methods include those described in U.S. Pat. No. 5,449,754 for synthesizing peptide arrays, as well as WO 98/41531 and the references cited therein for synthesizing polynucleotides (specifically, DNA). In situ methods also include photolithographic techniques such as described, for example, in WO 91/07087, WO 92/10587, WO 92/10588, and U.S. Pat. No. 5,143,854. The deposition methods basically involve depositing biopolymers at predetermined locations on a substrate which are suitably activated such that the biopolymers can link thereto. Biopolymers of different sequence may be deposited at different feature locations on the substrate to yield the completed array. Washing or other additional steps may also be used. Procedures known in the art for deposition of polynucleotides, particularly DNA such as whole oligomers or cDNA, are described, for example, in U.S. Pat. No. 5,807,522 (touching drop dispensers to a substrate), and in PCT publications WO 95/25116 and WO 98/41531, and elsewhere (use of an ink jet type head to fire drops onto the substrate).

In array fabrication, the quantities of DNA available for the array are usually very small and expensive. Sample quantities available for testing are usually also very small and it is therefore desirable to simultaneously test the same sample against a large number of different probes on an array. These conditions require the manufacture and use of arrays with large numbers of very small, closely spaced features.

The arrays, when exposed to a sample, will exhibit a binding pattern. The array can be interrogated by observing this binding pattern by, for example, labeling all polynucleotide targets (for example, DNA) in the sample with a suitable label (such as a fluorescent compound), scanning an interrogating light across the array and accurately observing the fluorescent signal from the different features of the array. Assuming that the different sequence polynucleotides were correctly deposited in accordance with the predetermined configuration, then the observed binding pattern will be indicative of the presence and/or concentration of one or more polynucleotide components of the sample. Peptide arrays can be used in a similar manner. Techniques for scanning arrays are described, for example, in U.S. Pat. No. 5,763,870 and U.S. Pat. No. 5,945,679. However, the signals detected from respective features emitted in response to the interrogating light, may be other than fluorescence from a fluorescent label. For example, the signals may be fluorescence polarization, reflectance, or scattering, as described in U.S. Pat. No. 5,721,435.

Array scanners typically use a laser as an interrogating light source, which is scanned over the array features. Particularly in array scanners used for DNA sequencing or gene expression studies, a detector (typically a fluorescence detector) with a very high light sensitivity is normally desirable to achieve maximum signal-to-noise in detecting hybridized molecules. At present, photomultiplier tubes ("PMTs") are still the detector of choice although charge coupled devices ("CCDs") can also be used. PMTs are typically used for temporally sequential scanning of array features, while CCDs permit scanning many features in parallel.

Laser output power in such array scanners may tend to drift over time. As described in U.S. Pat. No. 5,763,870, it is known to provide an integral power regulation sensor for a laser which is used to monitor laser output power. The power sensors (that is, laser light illuminance sensors) are connected to current-regulating circuitry that varies the supply current to the laser and responds to changes in output power. For gas lasers, the power sensors may be mounted internally and a beam splitter redirects a portion of the output beam energy to the power sensor, which may be a photodiode. For semiconductor lasers, the power sensor may be formed on the same substrate as the semiconductor layers that define the laser device, such as described in U.S. Pat. Nos. 5,323,026 and 4,577,320. However, the present invention recognizes that for some types of gas lasers it may be difficult to reliably switch between two power levels quickly, and that for diode lasers changing the laser power may have the undesired side effect of changing the wavelength.

The present invention further realizes that strong signals may occur in response to the interrogating light, either from bright features or from other components (for example, fluorescence of the glue holding an array substrate in a housing). In PMTs and other detectors (such as CCDs) very strong signals that are (depending on the type of detector) either spatially and/or temporally close to weak signals, may undesirably affect the latter. For example, a PMT reading a very bright signal at a given time, may change its sensitivity for a short time after this, or on a CCD detector very bright pixels may bleed their charge into adjacent ones. Extremely strong signals may even damage either kind of (normally expensive) detector. In any event, the accurate detection of signals from an array being interrogated by the scanner may be in doubt due to such effects.

The present invention realizes that it would be desirable then, to provide a technique for scanning an addressable array which allowed for rapid correction in variations in power of an interrogating light. The present invention further realizes that it would be desirable if some means were provided during array scanning, to limit exposure of a detector to very strong signals generated by features or other sites in response to the interrogating light. Additionally, the present invention also realizes that during the typically rapid scanning of an array, some types of light sources may not respond sufficiently rapidly to changes in power input (as discussed above) to allow for the corrections of the present invention while maintaining high array scanning speeds.

SUMMARY OF THE INVENTION

The present invention then, provides a method for use with an addressable array of multiple features of different moieties. These moieties may, for example, be polynucleotides (such as DNA or RNA) of different sequences for different features. In the method, an interrogating light is scanned across the array. This scanning can be accomplished, for example, by moving the interrogating light relative to the array, moving the array relative to the interrogating light, or both. The interrogating light is generated from a variable optical attenuator through which light from a light source has passed, and which optical attenuator is responsive to a control signal to alter the power of the interrogating light. Signals from respective features emitted in response to the interrogating light, are detected. A power of the interrogating light from the variable optical attenuator is also detected. An attenuator control signal is adjusted to alter interrogating light power, which adjustment is based on the detected power. The power may be detected and altered at any convenient times. For example, the power may be detected and altered during the scanning step (such as during a transition of the interrogating light from one row to another in the case where the array includes rows of features which are scanned row by row).

In a second aspect, the interrogating light is scanned across multiple sites on an array package which includes the array, and which scanned sites include the features. Signals emitted from respective scanned sites in response to the interrogating light, are detected. The interrogating light power is adjusted for a first site (which may or may not be an array feature) on the array package during the array scan based on some characteristic of the first site, such as location of the first site or a determination that the emitted signal from the first site will be outside a predetermined range (for example, a lower or upper limit) absent the altering. For example, the interrogating light power may be reduced based on a determination that the emitted signal from the first site will exceed a predetermined value, or based on location of the first site. If the determination is used this can be based, for example, on the results of a pre-scan or on the signal emitted from the first site when the interrogating light initially illuminates the first site. A pre-scan can include scanning an interrogating light across multiple sites on the array package using a lower sensitivity than that used in the previously mentioned scan (sometimes referenced as the "main scan"). Lower sensitivity can be obtained by using a lower interrogating light power, or with an emitted signal detector of lowered light sensitivity. Signals emitted in response to this interrogating light are detected and the determination based on one or more of these signals obtained in the pre-scan. If interrogating light power is altered based on location of the first feature, this location can be based on a reading (machine or human) of an identification associated with the array package (such as an identification carried on the package).

In the second aspect, any alteration of the interrogating light power can be made using the results of a previously obtained calibration. In particular, the method may also include calibrating the interrogating light power versus a control signal, for a light system which provides the interrogating light of a power which varies in response to the control signal. Optionally, this calibration may be repeated before scanning and detection for each of multiple array packages. While various light systems may be used in the second aspect, a light system which includes a light source and an optical attenuator in the arrangement disclosed above, may for example be used.

The present invention further provides apparatus for executing methods of the present invention. In a first aspect, the apparatus includes the light source and variable optical attenuator, a scanning system to control scanning, an emitted signal detector, and a power detector to detect the power of the interrogating light. The apparatus also includes a system controller which receives input from, and controls the remainder of, the apparatus as required (including using location information or making determinations, as described above) such that the remainder of the apparatus can execute a method of the invention. For example, the system controller may adjust the optical attenuator control signal to alter interrogating light power, based on the power detected by the power detector. Such an apparatus can execute the first aspect of the method described above. In an alternative example, the system controller adjusts the interrogating light power for a first site on the array package during the array scan based on location of the first site or on a determination that the emitted signal from the first site will be outside a predetermined range absent alteration. Such an apparatus can execute the second aspect of the method described above. However, the system controller optionally, and preferably, receives input from, and controls the remainder of, the apparatus as required such that the same apparatus can execute both a method of the first and second aspects described above.

In one particular embodiment of the apparatus, the apparatus further includes a reader to machine read an identification carried on the array package. In this case, the system controller may determine the location of the first site based on the read identification. This determination can, for example, be made directly from data contained in the read identification or retrieved from a local or remote source using the identification.

The present invention further provides a computer program product for use in an apparatus of the present invention. Such a computer program product includes a computer readable storage medium having a computer program stored thereon which, when loaded into a computer of the apparatus, such as the controller, causes it to perform the steps required by the apparatus to execute a method of the present invention.

While the methods and apparatus have been described in connection with arrays of various moieties, such as polynucleotides or DNA, other moieties can include any chemical moieties such as biopolymers. Also, while the detected signals may particularly be fluorescent emissions in response to the interrogating light, other detected signals in response to the interrogating light can include polarization, reflectance, or scattering, signals. Also, the described methods in the present application can be used to alter the actual scanning pattern of the interrogating light (rather than, or in addition to altering the interrogating light power) on the array package, particularly based upon a read identification (such as a machine readable identification) carried on the array package. For example, the dimensions of the scanned area, and/or the number of scan lines and/or scan line spacing may be based on the read identification (with the required information being retrieved from the read ID or from a local or remote database).

The method, apparatus, and kits of the present invention can provide any one or more of the following or other benefits. For example, correction in the power of an interrogating light can be obtained. Also, exposure of a detector to very strong signals generated by features or other sites in response to the interrogating light, can be limited based on rapid altering of interrogating light power. This can avoid both detector damage and detector blinding (temporary, light-induced change of sensitivity) at high switching speeds with a simple apparatus. Further, alterations of interrogation light power may be obtained which may be faster than obtainable from altering power to some types of light sources, so that high array scanning rates can still be maintained.

BRIEF DESCRIPTION OF THE DRAWINGS

Embodiments of the invention will now be described with reference to the drawings, in which.

To facilitate understanding, the same reference numerals have been used, where practical, to designate similar elements that are common to the FIGS.

DETAILED DESCRIPTION OF THE INVENTION

Figure 1:
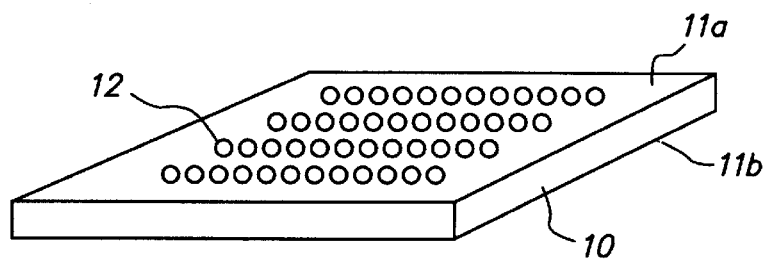
FIG. 1 is a perspective view of a substrate carrying a typical array, as may be used with, or part of, a package of the present invention.

Throughout the present application, unless a contrary intention appears, the following terms refer to the indicated characteristics. A "biopolymer" is a polymer of one or more types of repeating units. Biopolymers are typically found in biological systems and particularly include peptides or polynucleotides, as well as such compounds composed of or containing amino acid or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as analogs (whether synthetic or naturally occurring) of such sub-units. For example, a "biopolymer" includes DNA (including cDNA), RNA, oligonucleotides, and PNA and other oligonucleotides as described in U.S. Pat. No. 5,948, 902 and references cited therein (all of which are incorporated herein by reference), regardless of the source. An "oligonucleotide" generally refers to a polynucleotide of about 10 to 100 nucleotides (or other units) in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution). An "addressable array" includes any one or two dimensional arrangement of discrete regions (or "features") bearing particular moieties (for example, different polynucleotide sequences) associated with that region and positioned at particular predetermined locations on the substrate (each such location being an "address"). These regions may or may not be separated by intervening spaces. By one item being "remote" from another, is referenced that the two items are at least in different buildings, and may be at least one mile, ten miles, or at least one hundred miles apart. An array "package" may be the array plus only a substrate on which the array is deposited, although the package may include other features (such as a housing). A "chamber" references an enclosed volume (although a chamber may be accessible through one or more ports). It will also be appreciated that throughout the present application, that words such as "top", "upper", and "lower" are used in a relative sense only. "Fluid" is used herein to reference a liquid. "Venting" or "vent" includes the outward flow of a gas or liquid. Reference to a singular item, includes the possibility that there are plural of the same items present. All patents and other cited references are incorporated into this application by reference.

Figure 2:
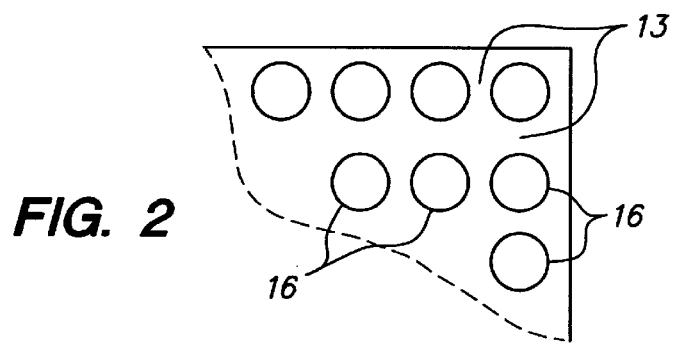
FIG. 2 is an enlarged view of a portion of FIG. 1 showing some of the identifiable individual regions of a single array of FIG. 1.
Figure 3:
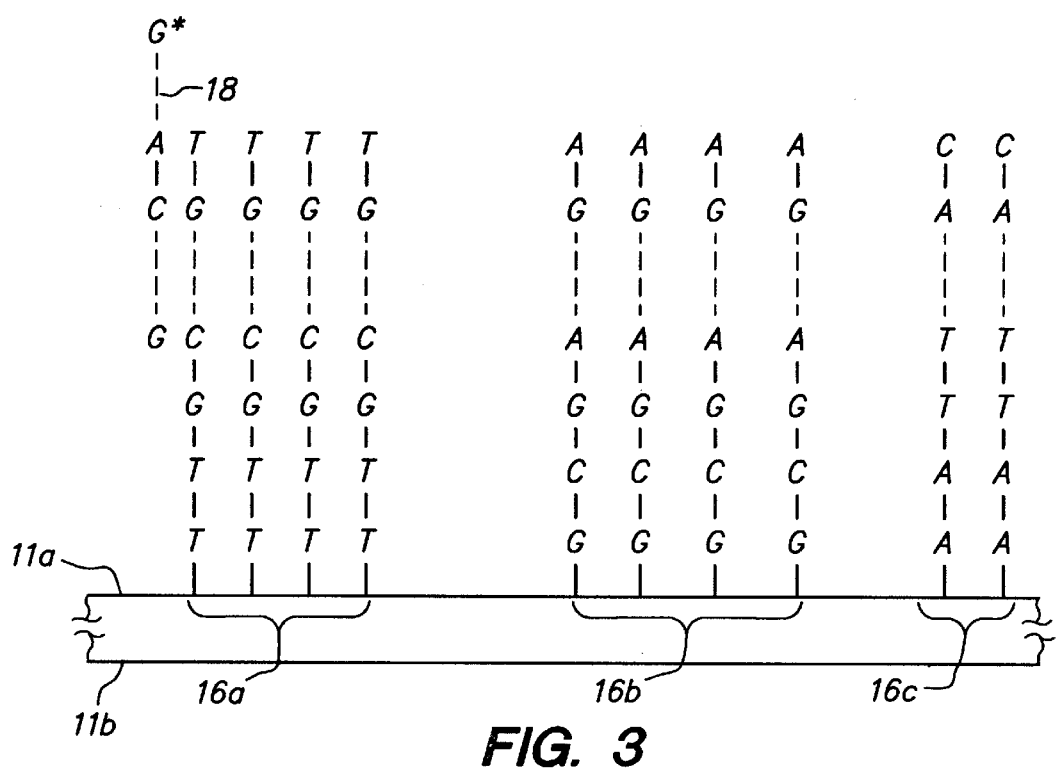
FIG. 3 is an enlarged cross-section of a portion of FIG. 2.

Referring first to FIGS. 1–3, a contiguous planar transparent substrate 10 carries multiple features 16 disposed across a first surface 11a of substrate 10 and separated by areas 13. Features 16 are disposed in a pattern which defines the array. A second surface 11b of substrate 10 does not carry any features. Substrate 10 may be of any shape although the remainder of the package of the present invention may need to be adapted accordingly. A typical array may contain at least ten features 16, or at least 100 features, at least 100,000 features, or more. All of the features 16 may be different, or some or all could be the same. Each feature carries a predetermined moiety or mixture of moieties which in the case of FIGS. 1–3 is a polynucleotide having a particular sequence. This is illustrated schematically in FIG. 3 where regions 16 are shown as carrying different polynucleotide sequences. Arrays of FIGS. 1–3 can be manufactured by in situ or deposition methods as discussed above. In use, a feature can detect a polynucleotide of a complementary sequence by hybridizing to it, such as polynucleotide 18 being detected by feature 16a in FIG. 3 (the "*" on polynucleotide 18 indicating a label such as a fluorescent label). Use of arrays to detect particular moieties in a sample (such as target sequences) are well known.

Figure 4:
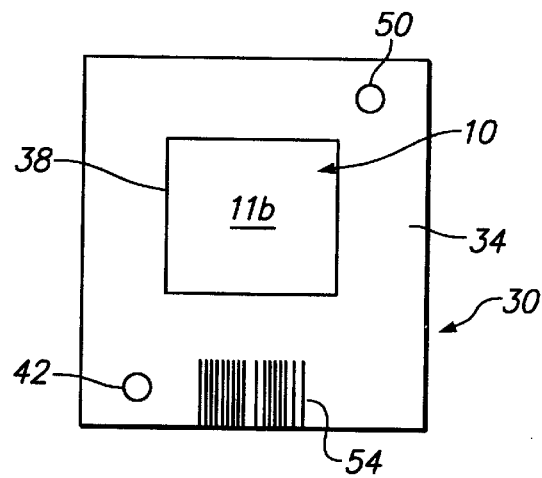
FIG. 4 is a front view of an array package in the form of a cartridge.

Referring now to FIG. 4 an array package 30 includes a housing 34 which has received substrate 10 adjacent an opening. Substrate 10 is sealed (such as by the use of a suitable adhesive) to housing 34 around a margin 38 with the second surface 11b facing outward. Housing 34 is configured such that housing 34 and substrate 10, define a chamber into which features 16 of array 12 face. This chamber is accessible through resilient septa 42, 50 which define normally closed ports of the chamber. Array package 30 preferably includes an identification ("ID") 54 of the array. The identification 54 may be in the form of a bar code or some other machine readable code applied during the manufacture of array package 30. Identification 54 may itself contain instructions for a scanning apparatus that the interrogating light power for at least a first site of the sites to be scanned and of specified location on array package 30 should be altered (typically, decreased). These instructions are typically based on the expectation that the emitted signals from those sites will be too bright or that those sites are not of interest (for example, they are off the area covered by the array). The specified sites (specified by location on array package 30) can be particular ones of features 16 or can be other sites on array package 30 such as margin 38 from which, for example, unduly bright fluorescence from an adhesive might be expected, or regions off the area covered by the array and hence are not of interest (and hence the instructions describe the area to be scanned). Alternatively, identification 54 may be simply a unique series of characters which is also stored in a local or remote database in association with the foregoing location information. Such a database may be established by the array manufacturer and made accessible to the user (or provided to them as data on a portable storage medium).

It will be appreciated though, that other array packages may be used. For example, the array package may consist only of the array of features 16 on substrate 10 (in which case ID 54 can be applied directly to substrate 10). Thus, an array package need not include any housing or closed chamber.

The components of the embodiments of the package 30 described above, may be made of any suitable material. For example, housing 34 can be made of metal or plastic such as polypropylene, polyethylene or acrylonitrile-butadiene-styrene ("ABS"). Substrate 10 may be of any suitable material, and is preferably sufficiently transparent to the wavelength of an interrogating and array emitted light, as to allow interrogation without removal from housing 34. Such transparent and non-transparent materials include, for flexible substrates: nylon, both modified and unmodified, nitrocellulose, polypropylene, and the like. For rigid substrates, specific materials of interest include: glass; fused silica, silicon, plastics (for example, polytetrafluoroethylene, polypropylene, polystyrene, polycarbonate, and blends thereof, and the like); metals (for example, gold, platinum, and the like). The first surface 11a of substrate 10 may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto (for example, conjugated), The materials from which substrate 10 and housing 34 (at least the portion facing toward the inside of chamber 36) may be fabricated should ideally themselves exhibit a low level of binding during hybridization or other events.

Figure 5:
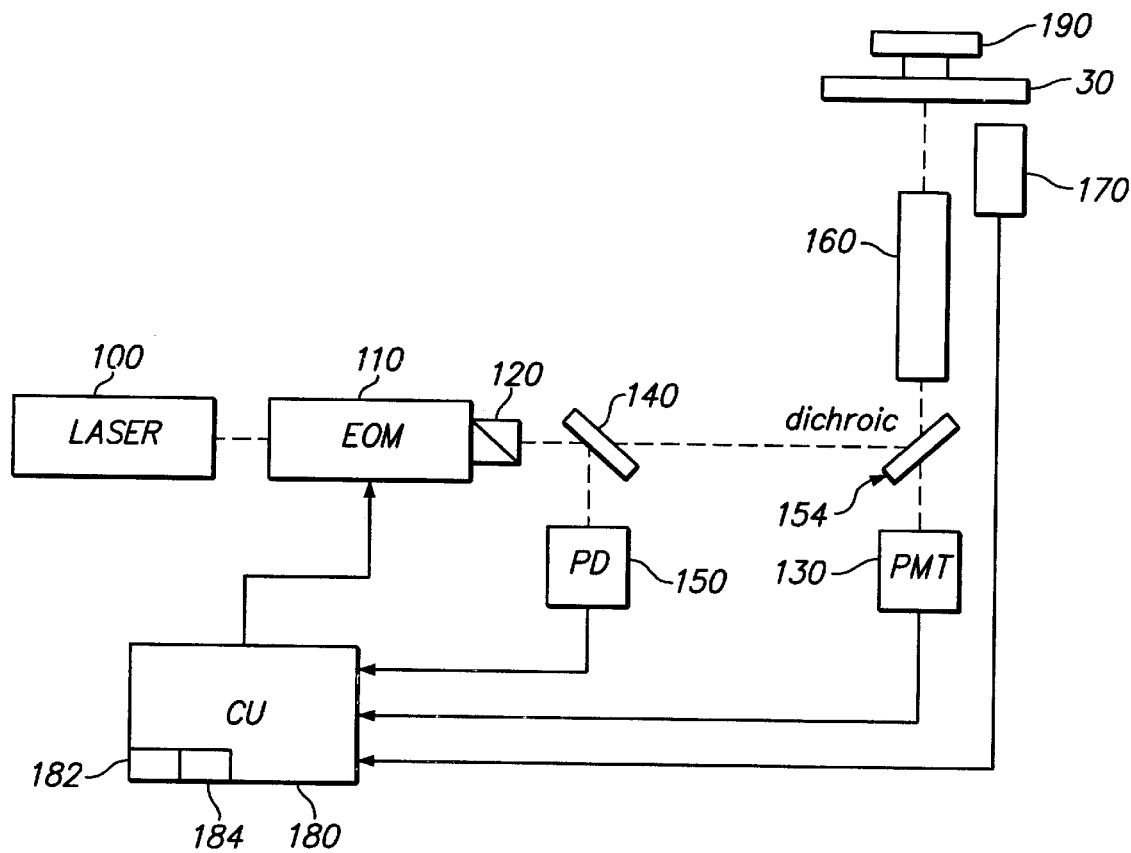
FIG. 5 illustrates an apparatus of the present invention.

Referring to FIG. 5, an apparatus of the present invention (which may be generally referenced as an array "scanner") is illustrated with an array package 30 mounted therein. A light system provides light from a laser 100 which passes through an electro-optic modulator (EOM)110 with attached polarizer 120. A control signal in the form of a variable voltage applied to the EOM 110 by the control unit (CU) 180 changes the polarization of the exiting light which is thus more or less attenuated by the polarizer 120. Thus, EOM 110 and polarizer 120 together act as a variable optical attenuator which can alter the power of an interrogating light spot exiting from the attenuator. A small portion of the transmitted light is reflected off a beamsplitter 140 to a photodiode or other power detector 150 (which therefore acts as an interrogating light power detector). The resulting signal is fed into the control unit 180. The remainder of the light transmitted by beamsplitter 140 is in this case reflected off a dichroic beamsplitter 154 and focused onto the array of array package 30 using optical components in beam focuser/scanner 160. Light emitted from features 16 in response to the interrogating light, for example by fluorescence, is imaged, for example, using the same optics in focuser/scanner 160, and passes through the dichroic beamsplitter 154 and onto a detector (PMT) 130. More optical components (not shown) may be used between the dichroic and the PMT (lenses, pinholes, filters, fibers etc.) and the detector 130 may be of various different types (e.g. a photo-multiplier tube (PMT) or a CCD or an avalanche photodiode (APD)). A scanning system causes the interrogating light spot to be scanned across multiple sites on an array package 30 received in the apparatus, which sites include at least the multiple features 16 of the array. In particular the scanning system is typically a line by line scanner, scanning the interrogating light in a line across the array package 30, then moving ("transitioning") the interrogating light to begin scanning a next row, scanning that next row, and repeating the foregoing procedure row after row. The scanning system can be a beam scanner within beam focuser/scanner 160 which moves the interrogating light across a stationary array package 30, or can be a transporter 190 which moves array package 30 in relation to a stationary interrogating light beam, or may be a combination of the foregoing (for example, with beam focuser/scanner 160 scanning the interrogating light spot across a row of features 16 of the array, and with transporter 190 moving the array one row at a time such that beam focuser/scanner 160 can scan successive rows of features 16).

The apparatus of FIG. 5 may further include a reader 170 which reads an identification 54 from an array package 30. When identification 54 is in the form of a bar code, reader 170 may be a suitable bar code reader. However, as described below, instead of (or in addition to) reader 170, the apparatus may execute a pre-scan or use initially determined emitted signal data from sites on array package 30.

A system controller 180 of the apparatus is connected to receive signals emitted in response to the interrogating light from emitted signal detector 130, signals indicating detected power from detector 150, and signals indicating a read identification from reader 170, and to provide the control signal to EOM 110. Controller 180 may also analyze, store, and/or output data relating to emitted signals received from detector 130 in a known manner. Controller 180 may include a computer in the form of a programmable digital processor, and include a media reader 182 which can read a portable removable media (such as a magnetic or optical disk), and a communication module 184 which can communicate over a communication channel (such as a network, for example the internet or a telephone network) with a remote site (such as a database at which information relating to array package 30 may be stored in association with the identification 54). Controller 180 is suitably programmed to execute all of the steps required by it during operation of the apparatus, as discussed further below. Alternatively, controller 180 may be any hardware or hardware/software combination which can execute those steps.

Figure 6:
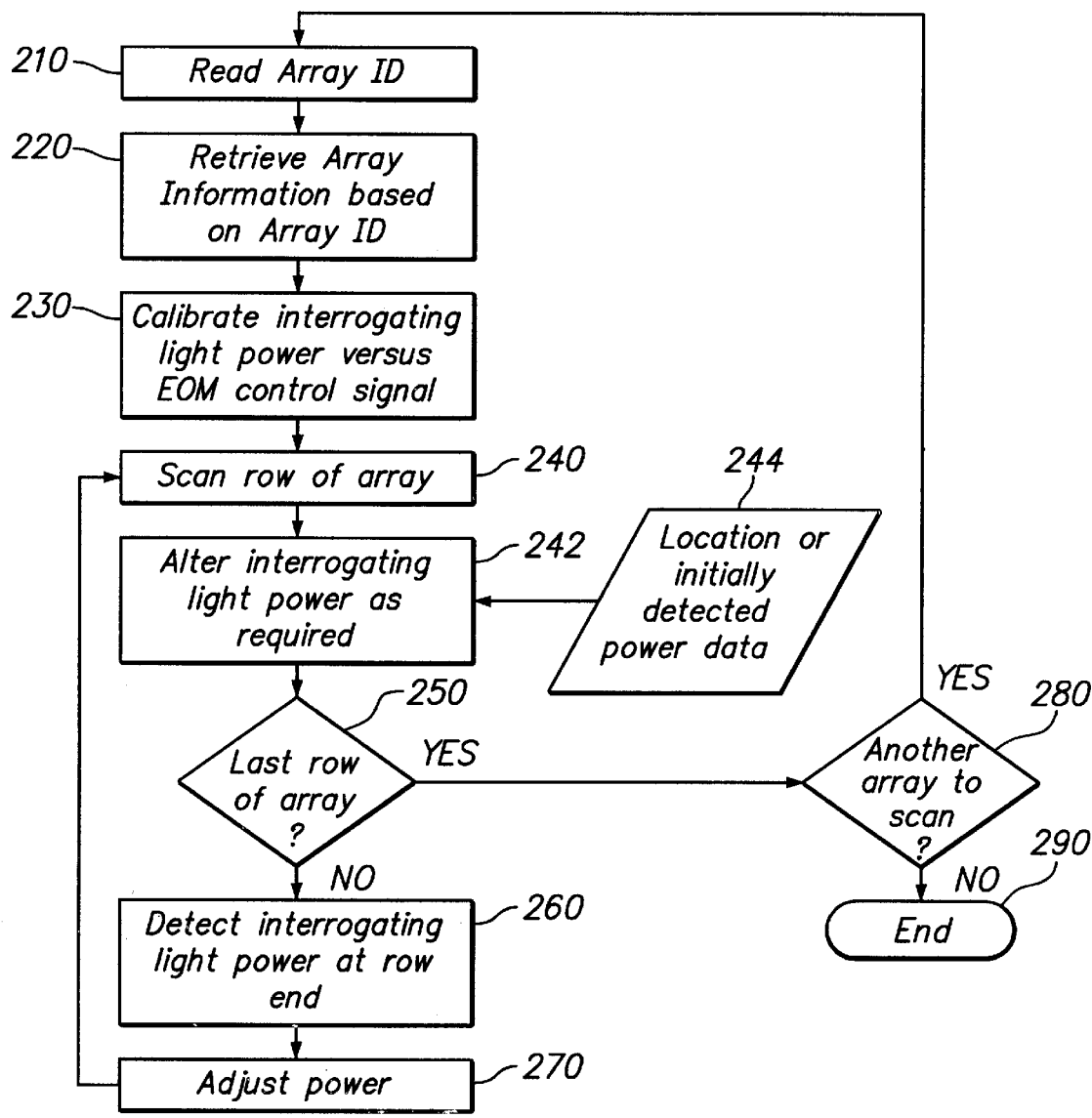
FIG. 6 is a flowchart illustrating a method of the present invention.

In one mode of operation, the array in package 30 is typically first exposed to a liquid sample introduced into the chamber through one of the septa 42, 50. The array may then be washed and scanned with a liquid (such as a buffer solution) present in the chamber and in contact with the array, or it may be dried following washing. Referring in particular to FIG. 6 following a given array package 30 being mounted in the apparatus, reader 170 automatically (or upon operator command) reads (210) array ID 54. Controller 180 can then use this ID 54 to retrieve (220)

locations on package 30 at which the interrogating light power should be altered (typically, reduced). Such information may be retrieved directly from the contents of ID 54 when ID 54 contains such information. Alternatively, ID 54 may be used to retrieve such information from a database containing the ID in association with such information. Such a database may be a local database accessible by controller 180 (such as may be contained in a portable storage medium in drive 182 which is associated with package 30, such as by physical association with package 30 when received by the user, or by a suitable identification), or may be a remote database accessible by controller 180 through communication module 184 and a suitable communication channel (not shown).

The interrogating light power may be calibrated (230) versus a control signal. Specifically, this is done by calibrating EOM 110 before or after the steps 210, 230. In particular, the transmission of the EOM 110 is controlled using a high voltage differential input from controller 180. For example, a voltage differential of 296 volts may cause a minimum power output, while a voltage differential of 104 volts may cause a maximum power output. The power as a function of differential voltage is roughly sinusoidal with an offset from zero and scaling that varies with time and temperature. The voltage differential is the difference between the voltage at a first terminal A and the voltage at second terminal B of EOM 110. For easy transition between high and low transmission states, terminal A may be held constant while terminal B may be toggled between a high voltage state and ground. For example, terminal A may be set to 296 volts, and terminal B switched between ground and 192 volts. Other approaches are conceivable. When a scan is initiated, terminal B is set to ground. Then terminal A is swept from 0 to 500 volts. The voltage at terminal A is set to where the output power reaches a local minimum. After that, terminal B is swept from 0 to 500 volts. The power output values for given voltages at terminal B will be recorded by controller 180 (which may include suitable analog/digital converter for the output of photodiode detector 150). Controller 180 will be looking for a specific slope to set the maximum output power. If the maximum power setting is at a local maximum and the output power drops, there is no way of telling which direction it went, and thus how to correct for it. By looking for a specific slope near the peak, a small power fluctuation can be readily converted into a linear power correction.

Next, the scanning system scans in a line across a row of array features 16 in the manner already described. During such a row scan, the EOM 110 is controlled by controller 180 to alter (for example, reduce or increase) the interrogation light power for at least a first site of the scanned sites on package 30 as required by location data retrieved based on ID 54. As already mentioned, the one or more of such sites can be features 16, margin 38, or some other site. By "reduce" or "increase" in this context is referenced that the interrogation power for the specified site is less, or more, respectively, than for another site or sites (usually other previously interrogated features).

However, the location of such first sites can be determined by means other than from ID 54 and thus steps 210, 220 can be omitted. For example, such site information can be obtained during a pre-scan of package 30 executed before the above described main scan. In such a pre-scan the same line-by-line scanning procedure as described above is used, but with the apparatus adjusted for a lower sensitivity than used in the above described main scan, to identify any sites at which the emitted signal may be outside a predetermined range (typically, an emitted signal which will exceed a predetermined limit for detector 130) when the higher apparatus sensitivity of the main scan is used. During the subsequent main scan controller 180 alters interrogating light power for one or more such first sites based on the emitted signals obtained during the pre-scan. In another alternative arrangement, interrogating light power can be altered dynamically for one or more first sites, with controller 180 altering interrogating light power at any site based on detector 130 detecting an emitted signal from the first site when the interrogating light initially illuminates the first site during that same main scan. For example, feedback may be provided that reduces the laser power transmitted through the polarizer 120 in such a way that the signal increases as the square root of the number of molecules illuminated above a certain threshold rather than proportional to the number of molecules as it would otherwise do. However, the finite response time of any feedback system may produce possibly relevant artifacts if rapid signal changes occur (for example, when scanning across the edge of a feature 16). This can be compensated for by ignoring the corresponding pixels in the analysis if needed (wherein a pixel is typically a subset of a site).

In another alternative for determining the location of first sites of a type which are regions outside the array area, array package 30 can be provided with suitable markings positioned just outside the array area. These can be detected by detector 130 and are interpreted by controller 180 as indicating that all sites beyond such markings are outside the scan area and hence are sites which need not be scanned.

When the dynamic adjustment of interrogating light power is used, the signal versus brightness curve becomes very non-linear. However this need not be visible in data acquired as the signal is normally digitized and levels can be chosen such that the analog to digital converter saturates at levels lower than those at which the protection circuit (controller 180 and EOM 110) starts to reduce the amount of laser light reaching the sample. The dynamic adjustment has the advantage over the pre-scan of requiring only one scan (for example, when protecting from impurities on the array), while the pre-scan approach has the advantage of capturing the entire range of features up to extremely bright ones. Both advantages can be obtained using ID 54 though, in the manner described above.

Returning to FIG. 6, regardless of the whether the data (244) is location data obtained based on ID 54 or obtained from a pre-scan, or initial power data, controller 180 will alter interrogating light power for one or more first sites as indicated by such data (244). When scanning of one row of features is completed the interrogating light spot will scan off the array somewhat. By scanning "off" the array in this context is referenced that there are no more features 16 in the direction of the line along which the interrogating light spot has been scanning. If it is determined (250) that there is still one or more rows of the array to be scanned, controller 150 then detects interrogating light power (260) from detector 150 and, when the detected power does not equal a predetermined target power ("nominal" power), signals EOM 110 so as to adjust (270) the power to the target. Such a procedure corrects for any drift in output power from laser 100 due to temperature or other fluctuations. Such a checking and correction is preferably made during the relatively longer period of a transition from scanning one row to another (that is, the period where scanning features of one row has ended, until the period where scanning features of another row begins). This allows power fluctuations due to the corrections to be restricted to non-critical areas. Further, relatively little drift will likely occur during the scanning of a given row. Laser 100 and EOM 110 operating variations while the light source output is at it's minimum are normally not relevant since they constitute only minor fluctuations of a quantity (output power at minimum transmission) that is already small. At the minimum of transmission, the change of transmission vs. voltage is zero to first order (first derivative). Hence it may be necessary to dither the voltage slightly to track the minimum (i.e. the voltage that results in minimum transmission) as it may drift, for example as a consequence of temperature changes. In some cases it may be desirable to have additional power levels at ones disposal (see for example, the implementation of the square-root function above). In these cases, one can calibrate the system by measuring, storing and using a table of transmission values versus voltages prior to a scan and possibly also using the derivatives calculated from these for second order corrections (for example, compensating for laser power fluctuations).

The next row is then scanned (240) with any alterations (242) in interrogating light power being executed as before. However, it will be appreciated that it is possible to adjust interrogating light power more frequently than just during the transition from one row to another (for example, when the scanning interrogating light spot is between features 16).

The above cycle is repeated until it is determined (250) that the last row of an array in package 30 has been scanned. If it is determined (280) that another array is to be scanned (such as by an operator pressing a "START" button or by a switch in the array holder detecting mounting of another array), the entire cycle is then repeated. Note that calibration (230) of EOM 110 before scanning each array corrects for any drifts in performance (for example due to temperature variations) between array scans. Further, use of an EOM 110 can allow for more rapid alteration of the interrogating light than may otherwise be possible by simply controlling power to some types of light sources, such as laser 100.

Note that a variety of geometries of the features 16 may be constructed other than the organized rows and columns of the array of FIGS. 1–3. For example, features 16 can be arranged in a series of curvilinear rows across the substrate surface (for example, a series of concentric circles or semi-circles of spots), and the like. Even irregular arrangements of features 16 can be used, at least when some means is provided such that during their use the locations of regions of particular characteristics can be determined (for example, a map of the regions is provided to the end user with the array). Furthermore, substrate 10 could carry more than one array 12, arranged in any desired configuration on substrate 10. While substrate 10 is planar and rectangular in form, other shapes could be used with housing 34 being adjusted accordingly. In many embodiments, substrate 10 will be shaped generally as a planar, rectangular solid, having a length in the range about 4 mm to 200 mm, usually about 4 mm to 150 mm, more usually about 4 mm to 125 mm; a width in the range about 4 mm to 200 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. However, larger substrates can be used. Less preferably, substrate 10 could have three-dimensional shape with irregularities in first surface 11a. In any event, the dimensions of housing 34 may be adjusted accordingly.

The apparatus of FIG. 5 can be constructed accordingly to scan array packages of the described structure.

Various modifications to the particular embodiments described above are, of course, possible. Accordingly, the present invention is not limited to the particular embodiments described in detail above.

What is claimed is:

1. A method comprising:
   (a) scanning an interrogating light across an addressable array of multiple features of different moieties, which interrogating light is generated from a variable optical attenuator through which light from a light source has passed and which optical attenuator is responsive to a control signal to alter the power of the interrogating light;
   (b) detecting signals from respective features emitted in response to the interrogating light;
   (c) detecting a power of the interrogating light from the variable optical attenuator; and
   (d) adjusting the attenuator control signal to alter interrogating light power, based on the detected power.

2. A method according to claim 1 wherein the multiple features comprise polynucleotides of different sequences.

3. A method according to claim 1 wherein the multiple features comprise DNA of different sequences.

4. A method according to claim 1 wherein the detected signals are fluorescent emissions from the features.

5. A method according to claim 1 wherein the power is detected and altered during step (a).

6. A method according to claim 5 wherein the interrogating light additionally scans across sites other than on the array, and wherein the interrogating light power is decreased when the interrogating light has scanned off the array.

7. A method according to claim 5 wherein the interrogating light is scanned row by row across the array features, and wherein the interrogating light power is altered during a transition of the interrogating light from one row to another.

8. A method comprising:
   (a) scanning an interrogating light across multiple sites on an array package including an addressable array of multiple features of different moieties, which scanned sites include multiple features of the array;
   (b) detecting signals from respective scanned sites emitted in response to the interrogating light; and
   (c) altering the interrogating light power for a first site on the array package during the array scan based on location of the first site;
   wherein the interrogating light power is reduced based on location of the first site.

9. A method according to claim 8 wherein the multiple features comprise polynucleotides of different sequences.

10. A method according to claim 8 wherein the multiple features comprise DNA of different sequences.

11. A method according to claim 8 additionally comprising reading an identification carried on the array package and determining the location of the first site based on the read identification.

12. A method according to claim 11 wherein the identification is machine read.

13. A method comprising:
   (a) scanning an interrogating light across multiple sites on an array package including an addressable array of multiple features of different moieties, which scanned sites include multiple features of the array;
   (b) detecting signals from respective scanned sites emitted in response to the interrogating light; and
   (c) altering the interrogating light power for a first site on the array package during the array scan based on location of the first site or on a determination that the emitted signal from the first site will be outside a predetermined range absent the altering;

the method additionally comprising, prior to steps (a) through (c), performing a pre-scan which includes:

scanning an interrogating light across multiple sites on the array package using a lower sensitivity than that used in step (a); and detecting signals from respective scanned sites emitted in response to the interrogating light;

wherein the interrogating light power is altered based on the determination that the emitted signal from the first site will be outside a predetermined range, which is based on the emitted signal obtained from the first site during the pre-scan.

14. A method comprising:

(a) scanning an interrogating light across multiple sites on an array package including an addressable array of multiple features of different moieties, which scanned sites include multiple features of the array;

(b) detecting signals from respective scanned sites emitted in response to the interrogating light; and (c) altering the interrogating light power for a first site on the array package during the array scan based on location of the first site or on a determination that the emitted signal from the first site will be outside a predetermined range absent the altering;

wherein the interrogating light power is reduced based on a determination that the emitted signal from the first site will exceed a predetermined value;

and wherein the first site is not an array feature.

15. An apparatus for interrogating an addressable array of multiple features of different moieties, comprising:

(a) a light source and a variable optical attenuator through which light from the source passes to provide an interrogating light, and which optical attenuator is responsive to a control signal to alter the power of the interrogating light;

(b) a scanning system which scans the interrogating light across the addressable array;

(c) a signal detector to detect signals from respective features emitted in response to the interrogating light;

(b) a power detector to detect the power of the interrogating light from the variable optical attenuator; and (c) a system controller which adjusts the optical attenuator control signal to alter interrogating light power, based on the detected power.

16. An apparatus according to claim 15 wherein the power detector and system controller co-operate to detect and adjust interrogating light power prior to scanning each of multiple arrays.

17. An apparatus according to claim 15 wherein the power detector and system controller co-operate to detect and adjust interrogating light power during scanning of the interrogating light across the array.

18. An apparatus according to claim 15 wherein the system controller decreases the power when the scanning system causes the interrogating light to scan off the array.

19. An apparatus according to claim 18 wherein the scanning system causes the interrogating light to scan row by row across the array features, and wherein the power is adjusted during a transition of the interrogating light from one row to another.

20. An apparatus for interrogating an addressable array of multiple features of different moieties, carried by an array package, comprising:

(a) a light system which provides an interrogating light of variable power in response to a control signal;

(b) a scanning system which scans the interrogating light across multiple sites on the array package, which scanned sites include multiple features of the array;

(c) a signal detector which detects signals from respective sites emitted in response to the interrogating light; and (d) a system controller which adjusts the interrogating light power for a first site on the array package during the array scan based on location of the first site.

21. An apparatus according to claim 20 wherein the system controller reduces the interrogating light power for the first site.

22. A method according to claim 20 additionally comprising a reader to machine read an identification carried on the array package, and wherein the system controller determines the location of the first site based on the read identification.

23. An apparatus according to claim 20 wherein the light system includes a light source and an optical attenuator through which light from the source passes to provide the interrogating light, and wherein the control signal comprises a signal for the optical attenuator which provides variable attenuation in response to the characteristic of the control signal.

24. An apparatus for interrogating an addressable array of multiple features of different moieties, carried by an array package, comprising:

(a) a light system which provides an interrogating light of variable power in response to a control signal;

(b) a scanning system which scans the interrogating light across multiple sites on the array package, which scanned sites include multiple features of the array;

(c) a signal detector which detects signals from respective sites emitted in response to the interrogating light; and (d) a system controller which adjusts the interrogating light power for a first site on the array package during the array scan based on location of the first site or on a determination that the emitted signal from the first site will be outside a predetermined range absent alteration;

wherein adjustment is based on the determination by the system controller, which is based on the emitted signal detected from the first site;

and wherein the system controller, prior to the array scan, additionally causes the apparatus to execute a pre-scan which includes:

scanning the interrogating light across multiple sites on the array package using a lower sensitivity than that used in step (a); and detecting at the detector, signals from respective scanned sites emitted in response to the interrogating light;

wherein the determination made by the system controller that the emitted signal from the first site during a scan is outside a predetermined range, is based on the emitted signal obtained from the first site during the pre-scan.

25. An apparatus for interrogating an addressable array of multiple features of different moieties, carried by an array package, comprising:

(a) a light system which provides an interrogating light of variable power in response to a control signal characteristic;

(b) a scanning system which scans the interrogating light across multiple sites on the array package, which scanned sites include multiple features of the array;

(c) a signal detector which detects signals from respective sites emitted in response to the interrogating light; and (d) a system controller which calibrates interrogating light power in response to the control signal characteristic, and which adjusts the interrogating light power for a first site on the array package during the array scan using the calibration, based on location of the first site or on a determination that the emitted signal from the first site will be outside a predetermined range;

wherein the controller repeats the calibration prior to each scanning of an array package.

26. An apparatus for interrogating an addressable array of multiple features of different moieties, carried by an array package, comprising:

(a) a light system which provides an interrogating light of variable power in response to a control signal characteristic;

(b) a scanning system which scans the interrogating light across multiple sites on the array package, which scanned sites include multiple features of the array;

(c) a signal detector which detects signals from respective sites emitted in response to the interrogating light; and (d) a system controller which calibrates interrogating light power in response to the control signal characteristic, and which adjusts the interrogating light power for a first site on the array package during the array scan using the calibration, based on location of the first site.

27. A computer program product for use on an apparatus for interrogating an addressable array of multiple features of different moieties by means of an interrogating light generated from a variable optical attenuator through which light from a light source has passed, and which optical attenuator is responsive to a control signal to alter the power of the interrogating light, the program product comprising: a computer readable storage medium having a computer program stored thereon which, when loaded into a computer of the apparatus performs the steps of:

(a) causing the interrogating light to scan across the addressable array;

(b) receiving an indication of interrogating light power from the variable optical attenuator; and (c) adjusting the attenuator control signal to alter interrogating light power, based on the detected power.

28. A computer program product according to claim 27 wherein the attenuator control signal is adjusted to decrease light power when the interrogating light has scanned off the array.

29. A computer program product for use on an apparatus for interrogating an addressable array of multiple features of different moieties by means of an interrogating light generated from a light system which provides an interrogating light of variable power in response to a control signal, the program product comprising: a computer readable storage medium having a computer program stored thereon which, when loaded into a computer of the apparatus performs the steps of:

(a) causing the interrogating light to scan across multiple sites on an array package including an addressable array of multiple features of different moieties, which scanned sites include multiple features of the array; and (b) adjusting the control signal to alter the interrogating light power for a first site on the array package during the array scan, based on location of the first site or on a determination that the emitted signal from the first site will be outside a predetermined range.

30. A computer program product according to claim 29 wherein the interrogating light power is reduced based on a determination that the emitted signal from the first site will exceed a predetermined value.

31. A computer program product according to claim 29 wherein the adjustment is based on location of the first site.

32. A computer program product according to claim 29 wherein the determination is based on an emitted signal detected from the first site.

* * * * *